(12) United States Patent
De Villiers et al.

(10) Patent No.: US 7,531,001 B2
(45) Date of Patent: May 12, 2009

(54) INTERVERTEBRAL PROSTHESIS

(75) Inventors: Malan De Villiers, Gauteng (ZA);
Ulrich Reinhard Hähnle, Johannesburg (DE)

(73) Assignee: SpinalMotion, Inc., Mountain View, CA (US)

( * ) Notice: Subject to any disclaimer, the term of this patent is extended or adjusted under 35 U.S.C. 154(b) by 0 days.

(21) Appl. No.: 11/084,224

(22) Filed: Mar. 18, 2005

(65) Prior Publication Data

US 2005/0251262 A1    Nov. 10, 2005

Related U.S. Application Data

(63) Continuation-in-part of application No. PCT/IB03/01529, filed on Apr. 24, 2003.

(30) Foreign Application Priority Data

Sep. 19, 2002   (ZA) .................. 2002/7517

(51) Int. Cl.
*A61F 2/44*   (2006.01)
(52) U.S. Cl. .................. 623/17.14; 623/17.15
(58) Field of Classification Search .... 623/17.11–17.16
See application file for complete search history.

(56) References Cited

U.S. PATENT DOCUMENTS

| | | | |
|---|---|---|---|
| 3,486,505 | A | 12/1969 | Morrison |
| 4,759,766 | A | 7/1988 | Buettner-Janz et al. |
| 4,759,769 | A | 7/1988 | Hedman et al. |
| 4,834,757 | A | 5/1989 | Brantigan |
| 4,863,477 | A | 9/1989 | Monson |
| 4,997,432 | A | 3/1991 | Keller |
| 5,035,716 | A | 7/1991 | Downey |
| 5,057,108 | A | 10/1991 | Shetty et al. |
| 5,071,437 | A | 12/1991 | Steffee |

(Continued)

FOREIGN PATENT DOCUMENTS

DE   3023353 A1   4/1981

(Continued)

OTHER PUBLICATIONS

WO 04/026187 A1, Hahnle, Apr. 1, 2004.*

(Continued)

*Primary Examiner*—Bruce E Snow
(74) *Attorney, Agent, or Firm*—Townsend and Townsend and Crew LLP

(57) ABSTRACT

An intervertebral prosthesis for insertion between adjacent vertebrae includes upper and lower prosthesis plates locatable against respective vertebrae and having opposing, concavely curved recesses therein, and a core located between the plates. The core has opposed, convexly curved surfaces received in the recesses of the plates to allow the plates to slide in articulated manner over the core. The opposed surfaces of the core and the recesses of the plates have cooperating spherical curvatures. The recess of each plate surrounds a locating peg projecting centrally from the base of the recess and is bounded by an annular rim, such that the annular rims of the plates are arranged to contact one another at a predetermined limit of sliding movement of the plates over the core. The peg locates loosely in an opening located centrally in a curved surface of the core, whereby the plates can slide over the core in all directions while the peg holds the core captive.

29 Claims, 4 Drawing Sheets

U.S. PATENT DOCUMENTS

| | | | |
|---|---|---|---|
| 5,122,130 A | 6/1992 | Keller | |
| 5,195,526 A | 3/1993 | Michelson | |
| 5,258,031 A | 11/1993 | Salib et al. | |
| 5,282,861 A | 2/1994 | Kaplan | |
| 5,314,477 A | 5/1994 | Marnay | |
| 5,370,697 A | 12/1994 | Baumgartner | |
| 5,401,269 A | 3/1995 | Buettner-Janz et al. | |
| 5,415,704 A | 5/1995 | Davidson | |
| 5,489,307 A | 2/1996 | Kuslich et al. | |
| 5,507,816 A | 4/1996 | Bullivant | |
| 5,534,030 A | 7/1996 | Navarro et al. | |
| 5,556,431 A | 9/1996 | Buttner-Janz | |
| 5,674,296 A | 10/1997 | Bryan et al. | |
| 5,676,701 A | 10/1997 | Yuan et al. | |
| 5,676,702 A | 10/1997 | Ratron | |
| 5,702,450 A | 12/1997 | Bisserie | |
| 5,797,909 A | 8/1998 | Michelson | |
| 5,824,094 A | 10/1998 | Serhan et al. | |
| 5,865,846 A | 2/1999 | Bryan et al. | |
| 5,888,226 A | 3/1999 | Rogozinski | |
| 5,899,901 A | 5/1999 | Middleton | |
| 5,899,911 A | 5/1999 | Carter | |
| 5,928,284 A | 7/1999 | Mehdizadeh | |
| 5,989,291 A | 11/1999 | Ralph et al. | |
| 6,001,130 A | 12/1999 | Bryan et al. | |
| 6,019,792 A | 2/2000 | Cauthen | |
| 6,022,376 A | 2/2000 | Assell et al. | |
| 6,039,763 A | 3/2000 | Shelokov | |
| 6,096,038 A | 8/2000 | Michelson | |
| 6,139,579 A | 10/2000 | Steffee et al. | |
| 6,143,033 A | 11/2000 | Paul et al. | |
| 6,146,421 A | 11/2000 | Gordon et al. | |
| 6,156,067 A | 12/2000 | Bryan et al. | |
| 6,162,252 A | 12/2000 | Kuras et al. | |
| 6,176,881 B1 | 1/2001 | Schar et al. | |
| 6,235,030 B1 | 5/2001 | Zuckerman et al. | |
| 6,261,296 B1 | 7/2001 | Aebi et al. | |
| 6,315,797 B1 | 11/2001 | Middleton | |
| 6,322,567 B1 | 11/2001 | Mittelstadt et al. | |
| 6,348,071 B1 | 2/2002 | Steffee et al. | |
| 6,368,350 B1 | 4/2002 | Erickson et al. | |
| 6,416,551 B1 | 7/2002 | Keller | |
| 6,447,544 B1 | 9/2002 | Michelson | |
| 6,478,800 B1 | 11/2002 | Fraser et al. | |
| 6,517,580 B1 | 2/2003 | Ramadan et al. | |
| 6,520,996 B1 | 2/2003 | Manasas et al. | |
| 6,527,804 B1 | 3/2003 | Gauchet et al. | |
| 6,562,047 B2 | 5/2003 | Ralph et al. | |
| 6,582,466 B1 | 6/2003 | Gauchet | |
| 6,592,624 B1 | 7/2003 | Fraser et al. | |
| 6,599,294 B2 | 7/2003 | Fuss et al. | |
| 6,607,558 B2 | 8/2003 | Kuras | |
| 6,610,092 B2 | 8/2003 | Ralph et al. | |
| 6,645,248 B2 * | 11/2003 | Casutt | 623/17.12 |
| 6,652,533 B2 | 11/2003 | O'Neil | |
| 6,666,866 B2 | 12/2003 | Mertz et al. | |
| 6,669,732 B2 | 12/2003 | Serhan et al. | |
| 6,682,562 B2 | 1/2004 | Viart et al. | |
| 6,689,132 B2 | 2/2004 | Biscup | |
| 6,706,068 B2 | 3/2004 | Ferree | |
| 6,712,825 B2 | 3/2004 | Aebi et al. | |
| 6,723,097 B2 | 4/2004 | Fraser et al. | |
| 6,726,720 B2 | 4/2004 | Ross et al. | |
| 6,740,118 B2 | 5/2004 | Eisermann et al. | |
| 6,770,095 B2 | 8/2004 | Grinberg et al. | |
| 6,814,737 B2 | 11/2004 | Cauthan | |
| 6,875,213 B2 | 4/2005 | Michelson | |
| 6,963,071 B2 | 11/2005 | Bristol | |
| 6,966,929 B2 * | 11/2005 | Mitchell | 623/17.11 |
| 6,994,727 B2 | 2/2006 | Khandkar et al. | |
| 7,025,787 B2 | 4/2006 | Bryan et al. | |
| 7,056,344 B2 | 6/2006 | Huppert et al. | |
| 7,060,073 B2 | 6/2006 | Frey et al. | |
| 7,179,294 B2 | 2/2007 | Eisermann et al. | |
| 7,182,784 B2 | 2/2007 | Evans et al. | |
| 2001/0016773 A1 | 8/2001 | Serhan et al. | |
| 2001/0029377 A1 | 10/2001 | Aebi et al. | |
| 2002/0035400 A1 * | 3/2002 | Bryan et al. | 623/17.15 |
| 2002/0045904 A1 | 4/2002 | Fuss et al. | |
| 2002/0068936 A1 | 6/2002 | Burkus et al. | |
| 2002/0128715 A1 | 9/2002 | Bryan et al. | |
| 2002/0198532 A1 | 12/2002 | Michelson | |
| 2003/0009224 A1 | 1/2003 | Kuras | |
| 2003/0045939 A1 | 3/2003 | Casutt | |
| 2003/0074076 A1 | 4/2003 | Ferree et al. | |
| 2003/0100951 A1 | 5/2003 | Serhan et al. | |
| 2003/0135277 A1 | 7/2003 | Bryan et al. | |
| 2003/0191536 A1 | 10/2003 | Ferree | |
| 2003/0199982 A1 | 10/2003 | Bryan | |
| 2003/0204261 A1 * | 10/2003 | Eisermann et al. | 623/17.14 |
| 2003/0208271 A1 | 11/2003 | Kuras | |
| 2004/0002761 A1 | 1/2004 | Rogers et al. | |
| 2004/0024407 A1 | 2/2004 | Ralph | |
| 2004/0024410 A1 | 2/2004 | Olson et al. | |
| 2004/0030391 A1 * | 2/2004 | Ferree | 623/17.16 |
| 2004/0073312 A1 | 4/2004 | Eisermann et al. | |
| 2004/0143270 A1 | 7/2004 | Zucherman et al. | |
| 2004/0176843 A1 | 9/2004 | Zubok et al. | |
| 2004/0215342 A1 | 10/2004 | Suddaby | |
| 2005/0021145 A1 | 1/2005 | de Villiers et al. | |
| 2005/0021146 A1 | 1/2005 | de Villiers et al. | |
| 2005/0043800 A1 | 2/2005 | Paul et al. | |
| 2005/0085917 A1 | 4/2005 | Marmay et al. | |
| 2005/0107881 A1 | 5/2005 | Alleyne et al. | |
| 2005/0149189 A1 | 7/2005 | Mokhter et al. | |
| 2005/0192586 A1 | 9/2005 | Zucherman et al. | |
| 2005/0192670 A1 | 9/2005 | Zubok et al. | |
| 2005/0197706 A1 | 9/2005 | Hovorka et al. | |
| 2005/0251262 A1 | 11/2005 | de Villiers et al. | |
| 2005/0261772 A1 | 11/2005 | Filippi et al. | |
| 2005/0267580 A1 | 12/2005 | Suddaby | |
| 2006/0004453 A1 | 1/2006 | Bartish et al. | |
| 2006/0025862 A1 | 2/2006 | de Villiers et al. | |
| 2006/0029186 A1 | 2/2006 | de Villiers et al. | |
| 2006/0030857 A1 | 2/2006 | de Villiers et al. | |
| 2006/0030862 A1 | 2/2006 | de Villiers et al. | |
| 2006/0036325 A1 * | 2/2006 | Paul et al. | 623/17.14 |
| 2006/0041313 A1 | 2/2006 | Allard et al. | |
| 2006/0069439 A1 * | 3/2006 | Zucherman et al. | 623/17.14 |
| 2006/0178744 A1 | 8/2006 | de Villiers et al. | |
| 2006/0293754 A1 | 12/2006 | de Villiers et al. | |
| 2007/0061011 A1 | 3/2007 | de Villiers et al. | |
| 2007/0282449 A1 | 12/2007 | de Villiers et al. | |
| 2008/0051900 A1 | 2/2008 | de Villiers et al. | |
| 2008/0051901 A1 | 2/2008 | de Villiers et al. | |

FOREIGN PATENT DOCUMENTS

| | | |
|---|---|---|
| EP | 0333990 A2 | 9/1989 |
| EP | 0560140 A1 | 9/1993 |
| EP | 0560141 A1 | 9/1993 |
| EP | 591712 A1 | 4/1994 |
| EP | 1142544 A1 | 10/2001 |
| EP | 1153582 A2 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1417940 A1 | 5/2004 |
| WO | WO 00/35384 | 6/2000 |
| WO | WO 01/01893 A1 | 1/2001 |
| WO | WO 2004/026187 A2 | 4/2004 |

| | | |
|---|---|---|
| WO | WO 2005/053580 A1 | 6/2005 |

OTHER PUBLICATIONS

Karin Buttner-Janz, The Development of the Artificial Disc, Introduction, 1989, pp. 1-18, Library of Congress Catalogue No. 92-75582, ISBN 0-9635430-0-8.

Wayne G. Hellier, et al., "Wear Studies for Development of an Intervertebral Disc Prosthesis," *Spine*, vol. 17 No. 6 Supplement pp. 86-96 (1992).

Choon-Ki Lee, MD, et al., "Impact Response of the Intervertebral Disc in a Finite-Element Model," *Spine* vol. 25, No. 19, pp. 2431-2439.

J.C. Le Huec et al., "Shock Absorption in Lumber Disc Prosthesis," *Journal of Spinal Disorders & Techniques*, vol. 16, No. 4, pp. 346-351.

International Search Report PCT/US05/26160 Jul. 21, 2005.

International Search Report of PCT Application No. PCT/US06/002263, dated Jul. 27, 2007.

* cited by examiner

INTERVERTEBRAL PROSTHESIS

CROSS-REFERENCES TO RELATED APPLICATIONS

The present application is a continuation-in-part of PCT/IB2003/001529, filed on Apr. 24, 2003, designating the United States, which claimed priority from South African application 2002/7517, filed on Sep. 19, 2002, the full disclosures of which are incorporated herein by reference.

BACKGROUND OF THE INVENTION

1. Field of the Invention

This invention relates to an intervertebral prosthesis.

In the event of damage to a spinal disc it is known practice to implant an intervertebral prosthesis surgically to replace the damaged organ. Several types of prosthesis for this purpose are known and in common use.

One type of known intervertebral prosthesis is sold by Waldemar Link GmbH & Co under the trade mark LINK® SB Charité. This prosthesis includes upper and lower prosthesis plates which locate against and engage the adjacent vertebral bodies, and a low friction core between the plates. The core has upper and lower convexly curved surfaces and the plates have corresponding, concavely curved recesses which cooperate with the curved surfaces of the core. This allows the plates to slide over the core to allow required spinal movements to take place. The curved recesses in the plates are surrounded by annular ridges which locate, at the limit of sliding movement of the plates over the core, in opposing peripheral channels surrounding the curved surfaces of the core.

This type of configuration is also described in EP 0 560 140 and EP 0 560 141 (both Waldemar Link GmbH & Co). However a drawback of such configurations is that the provision of the peripheral ribs and channels limits the areas available for bearing and sliding contact between the plates and core, and accordingly the loads which can be transmitted by the prosthesis. As a result of the relatively small bearing areas, it is believed that at least the core will be subject to rapid wear and have a relatively short life-span.

EP 0 560 141 also describes one alternative arrangement in which the curved surfaces of the core carry opposing, elongate keys that locate in elongate grooves in the plates and another alternative arrangement in which the plates have opposing elongate keys that locate in elongate grooves in the opposite curved surfaces of the core. These key and groove arrangements allow the plates to slide freely over the core, within the limits of the length of the grooves, in one plane only. Although allowance is made for some lateral play of the keys in the grooves, very little sliding movement of the plates over the core can take place in the orthogonal vertical plane, and this is considered to be a serious drawback of this design.

2. Description of the Background Art

European Patent Publications EP 0 560 140 and EO 0 560 141 have been discussed above. U.S. Patent Publications U.S. 2002/0035400 and U.S. 2002/0128715 describe intervertebral prostheses with center-posts received in passages in a core. The core possesses an annular flange structure engaged by extensions on the plates.

BRIEF SUMMARY OF THE INVENTION

According to the invention there is provided an intervertebral prosthesis for insertion between adjacent vertebrae, the prosthesis comprising upper and lower prosthesis plates locatable against the respective vertebrae and having opposing, concavely curved recesses therein and a core located between the plates, the core having opposed, convexly curved surfaces received in the recesses of the plates to allow the plates to slide in articulated manner over the core, characterized in that:

the opposed surfaces of the core and the recesses of the plates have cooperating spherical curvatures, the recess of a plate surrounds a locating peg projecting centrally from the base of the recess, and the peg locates loosely in an opening located centrally in a curved surface of the core, whereby the plates can slide over the core in all directions while the peg holds the core captive.

In some embodiments, only one of the plates, typically the operatively lower plate, includes a peg. In other embodiments, both plates include pegs, the pegs opposing one another and locating loosely in respective openings located centrally in the opposed curved surfaces of the core. In each embodiment it is preferred that each peg and the opening in which it locates are conical in shape.

According to another aspect of the invention there is provided a prosthesis plate for use in a prosthesis as summarized above, the prosthesis plate having a coarse surface locatable against a vertebra, an oppositely facing concavely curved surface which is complementary in shape to a convexly curved surface of a core of the prosthesis, characterized in that the concavely curved surface of the plate has a spherical curvature and in that the plate includes a conical locating peg extending centrally from the concavely curved surface, the peg being locatable loosely in a central opening in the convexly curved surface of the core.

According to yet another aspect of the invention there is provided a core for use in the prosthesis, the core comprising a one piece plastics body having operatively upper and lower curved surfaces, characterized in that the curved surfaces of the body are spherically curved and at least one of the surfaces has a central, conical opening therein dimensioned to receive a conical locating peg of a prosthesis plate loosely.

Other features of the invention are set forth in the appended claims.

BRIEF DESCRIPTION OF THE DRAWINGS

The invention will now be described in more detail, by way of example only, with reference to the accompanying drawings in which.

DETAILED DESCRIPTION OF THE INVENTION

Figure 1:
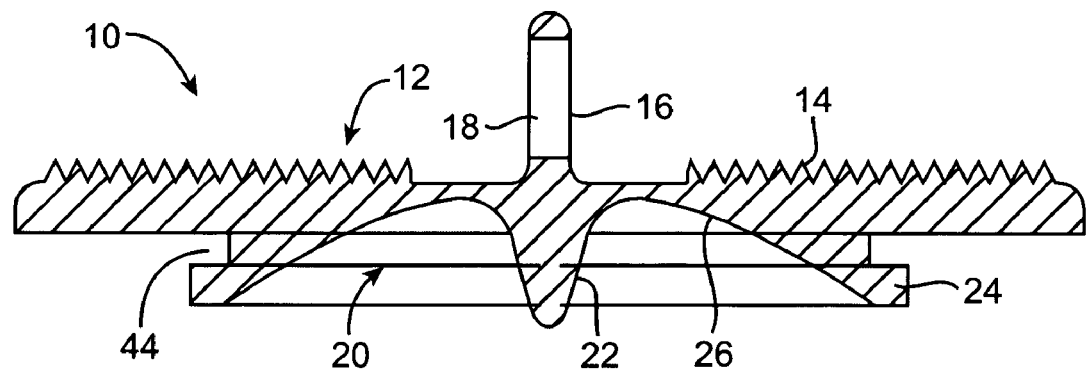
FIG. 1 shows a cross-sectional view of a prosthesis plate used in a prosthesis according to the invention.
Figure 2:
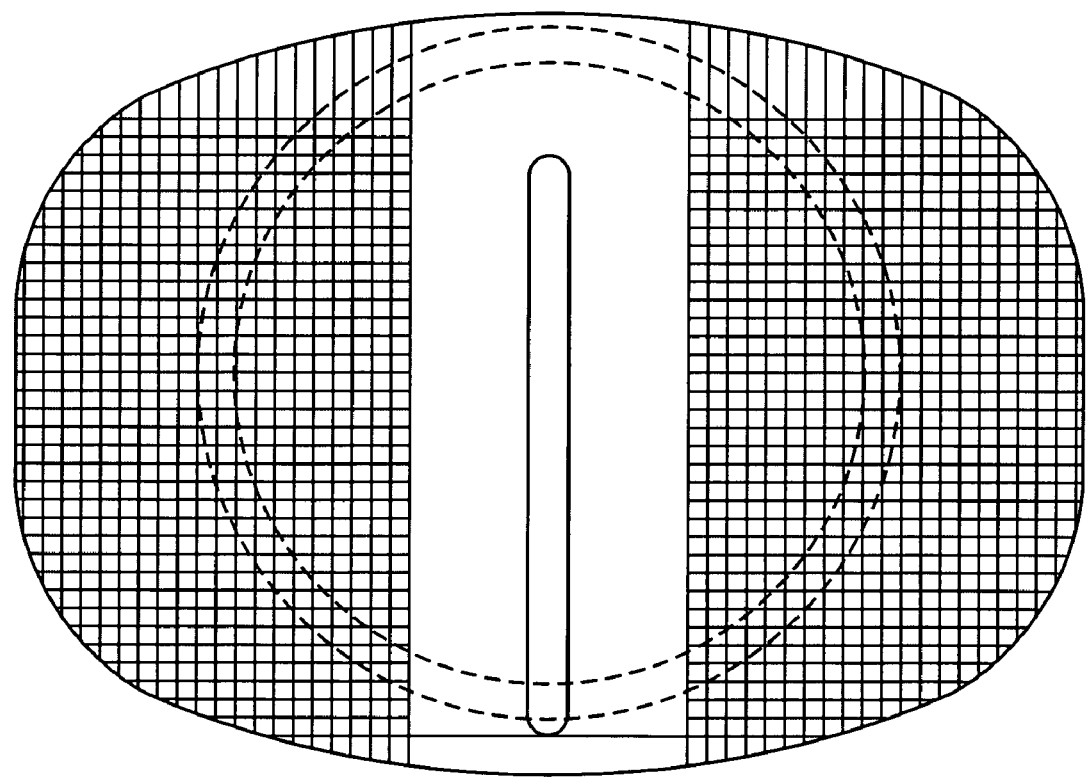
FIG. 2 shows a plan view of the prosthesis plate seen in FIG. 1.

The prosthesis plate 10 seen in FIGS. 1 and 2 may be formed from titanium, typically being formed in one piece of grade 5 titanium. Other suitable materials include titanium nitrides, cobalt chrome alloys, and ceramics. The prosthesis plate includes a major surface 12 which is machined to a coarse, serrated finish 14. Projecting from the surface 12 is an elongate fin 16 pierced by transverse holes 18. The opposite surface of the plate 10 is formed with a recess 20 surrounding a projecting conical peg 22 of round cross-section at the centre of the recess. The recess is bounded by an annular rim 24. The surface 26 of the recess is concavely, spherically curved and has a titanium nitride finish.

Figure 4:
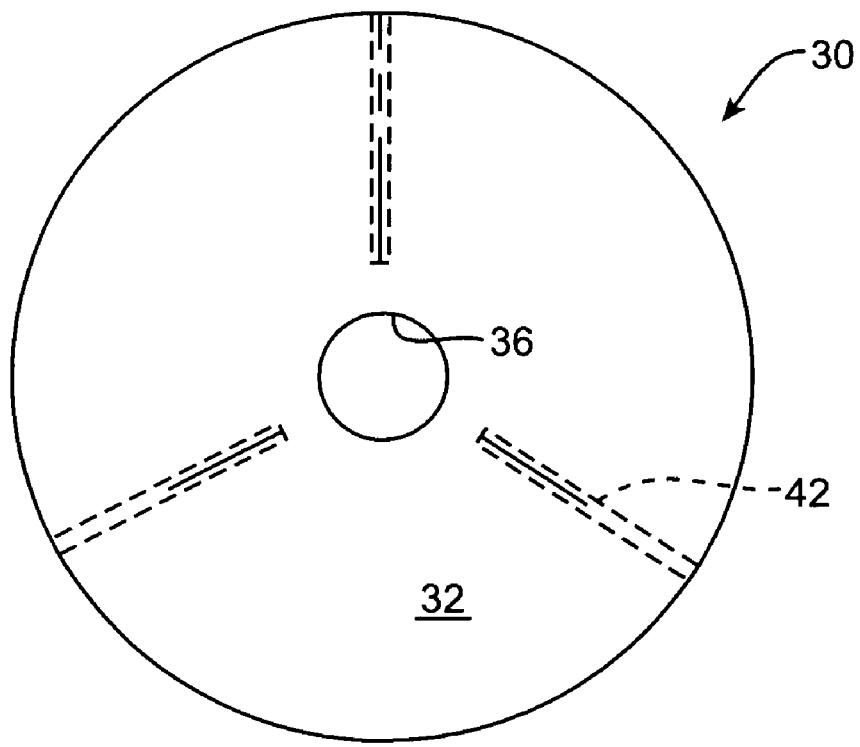
FIG. 4 shows a plan view of the core seen in FIG. 3.
Figure 5:
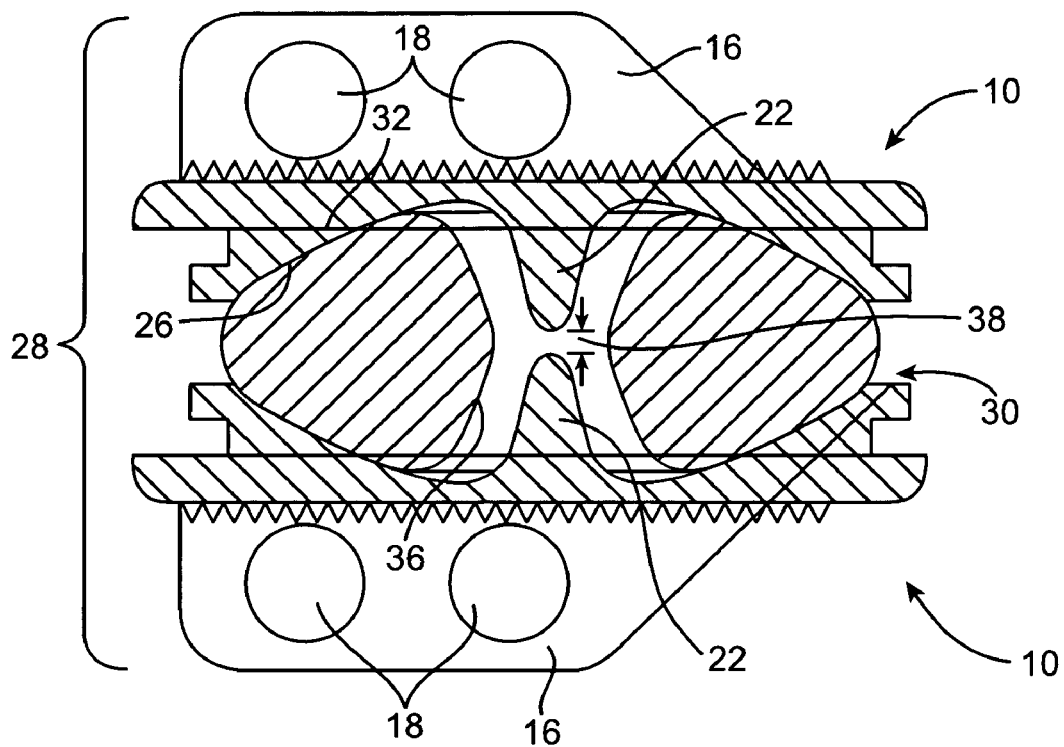
FIG. 5 shows a cross-sectional view of an intervertebral prosthesis according to a first embodiment of the invention in a neutral condition before articulation has taken place.
Figure 6:
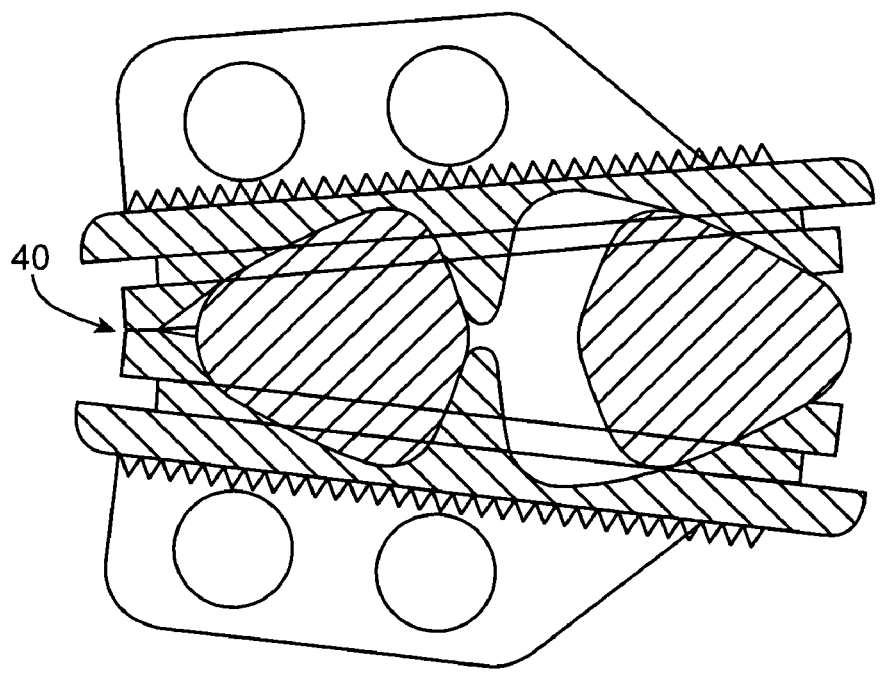
FIG. 6 shows the prosthesis of FIG. 5 articulated to a limit position.

A first embodiment of a prosthesis of the invention, indicated generally by the numeral 28 in FIGS. 5 and 6, includes a pair of identical prosthesis plates 10 arranged in opposition to one another. The prosthesis 28 also includes a core 30 illustrated in FIGS. 3 and 4. The core is made in one piece of a low friction plastics material, in this case a polyethylene known as Orthosol, but a variety of other high molecular weight polyethylenes might also find use. Alternatively, the core could be composed of a metal, such as cobalt chrome, or of a ceramic. The core is generally in the form of a circular, doughnut-shaped toroid and has identical upper and lower surfaces 32 which are convexly, spherically curved. The upper and lower surfaces 32 are formed centrally with conical openings 34, in this case forming the opposite ends of a circular cross-section passage 36 passing axially and centrally through the body of the core.

The core surfaces 32 and recess surface 26 have the same radius of curvature which is, in this case, 18 mm.

In the assembled prosthesis 28, the plates 10 are arranged in opposition to one another with the core 30 located between them. The pegs 22 of the plates locate in the openings 34, i.e. in the ends of the passage 36. The combined length of the pegs is less than the length of the passage 36, so the inner ends of the pegs are spaced apart from one another by a short distance 38, as shown in FIG. 5. The transverse dimension of each peg is, at all points along the length of the peg, considerably less than the diameter of the passage 36 at the corresponding point along the length of the passage.

The cooperating spherical surfaces 26 and 32 and the relative dimensions of the pegs 22 and the passage 36 allow the plates 10 to slide or articulate over the core through a fairly large range of angles and in all directions or degrees of freedom, including rotation about the central axis.

At a predetermined limit of articulated movement of the plates relative to the core, the rims 24 of the plates contact with one another as indicated by the numeral 40 in FIG. 6. Further articulation of the prosthesis 28 beyond this point is not possible. At the limit of articulation, the pegs 22 also come into abutment with the side of the passage 36, as also illustrated in FIG. 6.

It will also be noted in FIG. 6 that the openings 34 at the ends of the passage 36 are defined by similar cone angles to the pegs 22, so that contact between the pegs and the sides of the openings takes place complementally over virtually the entire length of each peg.

Throughout the range of possible articulation, the pegs 22 remain in the passage 36 and prevent the core from separating laterally from the plates 10. In other words, the core is held captive by the pegs during all possible articulations which can take place. In the illustrated embodiment, the plates 10 are limited to 12° of articulation before the rims 24 abut one another, i.e. 12° is the maximum articulation which can take place.

In the prosthesis 28 described above, the pegs 22 locate in a passage 32 which passes right through the core 30. It will however be understood that in other embodiments, the pegs could merely locate in blind recesses or openings in the opposite surfaces of the core without such openings actually being joined to one another to form a continuous passage.

Figure 7:
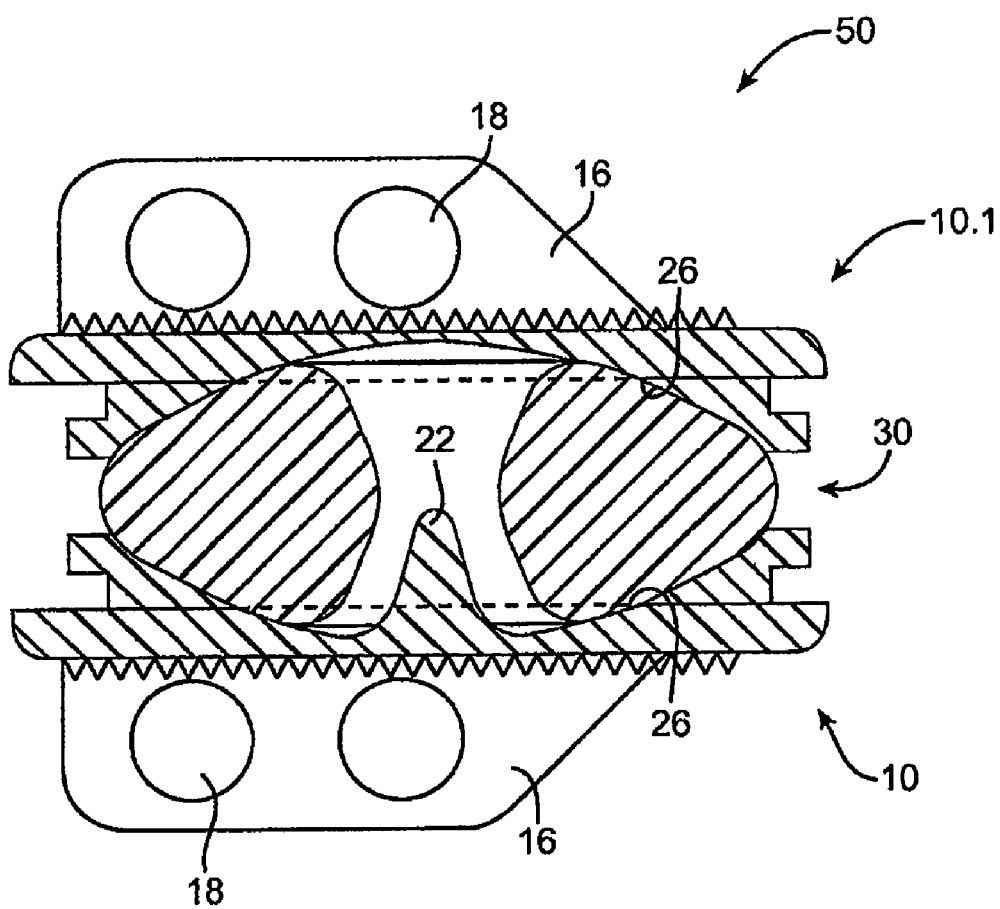
FIG. 7 shows a cross-sectional view of an intervertebral prosthesis according to a second embodiment of the invention.

FIG. 7 illustrates a prosthesis according to a second embodiment of the invention in a view similar to that of FIG. 5. In FIG. 7, components corresponding to components illustrated in the earlier Figures are indicated by the same reference numerals.

The lower prosthesis plate 10 in FIG. 7 is identical to the prosthesis plates of the first embodiment. However, the upper prosthesis plate, designated 10.1, has no central peg. Instead, the surface 26 is continuously, spherically curved. In all other respects the plate 10.1 is identical to the plate 10.

In the assembled prosthesis 50, the core is held captive by the action of the single peg 22 carried by the lower prosthesis plate 10. The core 30 is identical to the core described previously but once again it will be appreciated that the core could have a blind recess in its downwardly facing, curved surface 32 only to receive the single peg 22.

The prosthesis 28, 50 is surgically implanted between adjacent spinal vertebrae in place of a damaged disc. Those skilled in the art will understand that the adjacent vertebrae are forcibly separated from one another to provide the necessary space for insertion. The plates 10, 10.1 are slipped laterally into place between the vertebrae with their fins 16 entering slots cut in the opposing vertebral surfaces to receive them.

After insertion of the core between the opposing plates, the vertebra are allowed to move together to hold the assembled prosthesis in place.

The surfaces 12 of the plates 10, 10.1 locate against the opposing vertebrae and, with passage of time, firm connection between the plates and the vertebrae will be achieved as bone tissue grows over the serrated finish. Bone tissue growth will also take place about the fins 16 and through the holes 18 therein, further enhancing the connection which is achieved.

Figure 3:
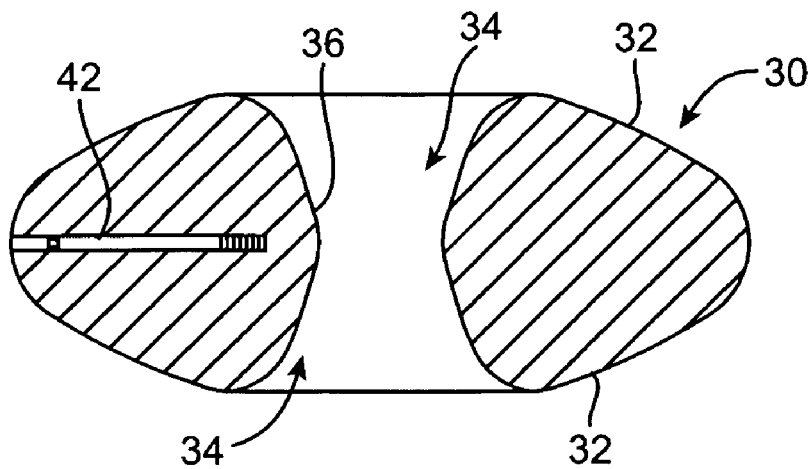
FIG. 3 shows a cross-sectional view of a core used in a prosthesis according to the invention.

Referring to FIGS. 3 and 4, the core 30 used in the embodiments described above is formed with narrow, angularly spaced, blind passages which accommodate titanium pins 42. The core itself is transparent to X-radiation and so would normally be invisible in a post-operative X-ray examination. The pins 42 serve as radiographic markers and enable the position of the core 30 to be ascertained during such examination.

Annular grooves 44 are provided in the plates 10, 10.1 to facilitate holding and manipulation of the prosthesis by appropriate instruments during placement into the intervertebral disc space.

Compared to known prostheses, the prostheses 28, 50 described above have a number of advantages, as follows:

1. The peg or pegs 22 hold the core captive and prevent it from slipping out sideways.
2. At a predetermined maximum limit of articulation, the rims 24 contact one another to prevent further articulation. At the same time, the peg or pegs 22 contact the sides of the openings 34, also preventing further articulation.
3. An acceptable bearing area of the plates on the core is obtained with the central peg/central opening configurations described above. This is particularly advantageous compared to prior art prostheses where the core has peripheral channels on its upper and lower surfaces to receive peripheral rims on the plates at the limit of articulation.

In practice, it may happen that there is imperfect alignment of the prosthesis plates. In the case of very poor alignment, the dual peg configuration of FIGS. 5 and 6 gives rise to the possibility that the pegs 22 are laterally offset from one another by a substantial distance. This can in turn lead to the undesirable consequence that the range of articulation which can be accommodated is unduly limited, and attempts to articulate past the limit could result in damage to the core by the misaligned pegs. In the embodiment of FIG. 7 the single peg can be received centrally by the core, thereby avoiding this potential problem.

The principles of the invention are applicable to prosthetic disc implants for lumbar vertebrae as well as cervical vertebrae. In the latter case, the fins 16 will typically be omitted.

What is claimed is:

1. An intervertebral prosthesis for insertion between adjacent vertebrae, the prosthesis comprising:
   upper and lower prosthesis plates locatable against respective vertebrae and having opposing, concavely curved recesses therein;
   a core located between the plates, the core having a height extending between the plates which is smaller than a width of the core in a direction perpendicular to the height, the core having opposed, convexly curved top and bottom surfaces received in the recesses of the plates to allow the plates to slide in an articulated manner over the core;
   wherein the opposed surfaces of the core and the recesses of the plates comprise cooperating curvatures;
   wherein each plate is bounded by an annular rim, such that the annular rims are arranged to contact one another at a predetermined limit of sliding movement of the plates over the core; and
   wherein each plate includes an empty annular groove adjacent to the rim, each groove configured and arranged to facilitate handling of the plate by instruments used to place the prosthesis in use.

2. A prosthesis according to claim 1, wherein at least the operatively lower plate includes a locating peg received loosely in an opening located centrally in a curved surface of the core, whereby the plates can slide over the core in all directions while the peg holds the core captive.

3. A prosthesis according to claim 2, wherein the peg and the opening in which it locates are conically shaped.

4. A prosthesis according to claim 3, wherein the core is a doughnut-shaped body and the central opening therein is provided by an end of a central passage extending axially through the body.

5. A prosthesis according to claim 1, wherein each plate includes a locating peg, the pegs opposing one another and locating loosely in respective openings located centrally in the opposed convexly curved surfaces of the core.

6. A prosthesis according to claim 5, wherein the core is a doughnut-shaped body and the central openings therein are provided by opposite ends of a central passage extending axially through the body.

7. A prosthesis according to claim 6, wherein the pegs are arranged to abut the side of the openings at the predetermined limit of sliding movement of the plates over the core.

8. A prosthesis according to claim 5, wherein the pegs and openings are complementally, conically shaped.

9. A prosthesis according to claim 1, wherein the plates have coarse surfaces to locate in use against the vertebrae.

10. A prosthesis according to claim 9, wherein the plates carry upstanding, elongate fins locatable in slots in the vertebrae.

11. A prosthesis according to claim 10, wherein holes are formed transversely through the fins.

12. An intervertebral prosthesis for insertion between adjacent vertebrae, the prosthesis comprising:
    upper and lower prosthesis plates locatable against respective vertebrae and having opposing, concavely curved recesses therein;
    a core located between the plates, the core having opposed, convexly curved surfaces received in the recesses of the plates to allow the plates to slide in an articulated manner over the core,
    a protrusion on at least one of the plates and corresponding opening on the core which hold the core captive and prevent the core from slipping out from between the plates;
    wherein each plate is bounded by an annular rim, such that the annular rims are arranged to contact one another at a predetermined limit of sliding movement of the plates over the core; and
    wherein each plate includes an empty annular groove adjacent to the rim, each groove configured and arranged to facilitate handling of the plate by instruments used to place the prosthesis in use.

13. A prosthesis according to claim 12, wherein at least the operatively lower plate includes a locating peg received loosely in an opening located centrally in a curved surface of the core, whereby the plates can slide over the core in all directions while the peg holds the core captive.

14. A prosthesis according to claim 13, wherein the peg and the opening in which it locates are conically shaped.

15. A prosthesis according to claim 13, wherein the core is a doughnut-shaped body.

16. A prosthesis according to claim 12, wherein each plate includes a locating peg, the pegs opposing one another and locating loosely in respective openings located centrally in the opposed convexly curved surfaces of the core.

17. A prosthesis according to claim 16, wherein the pegs are arranged to abut the side of the openings at the predetermined limit of sliding movement of the plates over the core.

18. A prosthesis according to claim 16, wherein the pegs and openings are complementally, conically shaped.

19. A prosthesis according to claim 12, wherein the plates have coarse surfaces to locate in use against the vertebrae.

20. A prosthesis according to claim 19, wherein the coarse surfaces comprise machined serrated finishes.

21. A prosthesis according to claim 12, wherein the plates carry upstanding, elongate fins locatable in slots in the vertebrae.

22. A prosthesis according to claim 21, wherein holes are formed transversely through the fins.

23. A prosthesis according to claim 1, wherein the plates are formed of titanium.

24. A prosthesis according to claim 1, wherein each plate has a serrated vertebra contacting surface.

25. A prosthesis according to claim 1, further comprising a protrusion on at least one of the plates and corresponding opening on the core which hold the core captive and prevent the core from slipping out sideways.

26. A prosthesis according to claim 1, wherein the core comprises metal.

27. An intervertebral prosthesis for insertion between adjacent vertebrae, the prosthesis comprising:
    upper and lower prosthesis plates locatable against respective vertebrae and having opposing, concavely curved recesses therein, the plates formed with empty annular grooves adjacent the rims to facilitate handling thereof by instruments used to place the prosthesis in use; and
    a core located between the plates, the core having opposed, convexly curved surfaces received in the recesses of the plates to allow the plates to slide in an articulated manner over the core;
    wherein the opposed surfaces of the core and the recesses of the plates comprise cooperating curvatures and wherein each plate is bounded by an annular rim, such that the annular rims are arranged to contact one another at a predetermined limit of sliding movement of the plates over the core.

28. An intervertebral prosthesis for insertion between adjacent vertebrae, the prosthesis comprising:

upper and lower prosthesis plates locatable against respective vertebrae and having opposing, concavely curved recesses therein; and a core located between the plates, the core having opposed, convexly curved surfaces received in the recesses of the plates to allow the plates to slide in an articulated manner over the core;

wherein the opposed surfaces of the core and the recesses of the plates comprise cooperating curvatures, at least the operatively lower plate including a locating peg received loosely in an opening located centrally in a curved surface of the core and wherein the plates can slide over the core in all directions while the peg holds the core captive;

wherein each plate is bounded by an annular rim, such that the annular rims are arranged to contact one another at a predetermined limit of sliding movement of the plates over the core; and wherein each plate includes an empty annular groove adjacent to the rim, each groove configured and arranged to facilitate handling of the plate by instruments used to place the prosthesis in use.

29. An intervertebral prosthesis for insertion between adjacent vertebrae, the prosthesis comprising:

upper and lower prosthesis plates locatable against respective vertebrae and having opposing, concavely curved recesses therein, each plate including a locating peg, the pegs opposing one another; and a core located between the plates, the core having opposed, convexly curved surfaces received in the recesses of the plates to allow the plates to slide in an articulated manner over the core, openings located centrally in the opposed convexly curved surfaces of the core, the pegs locating loosely in the respective openings;

wherein the opposed surfaces of the core and the recesses of the plates comprise cooperating curvatures and wherein each plate is bounded by an annular rim, such that the annular rims are arranged to contact one another at a predetermined limit of sliding movement of the plates over the core; and wherein each plate includes an empty annular groove adjacent to the rim, each groove configured and arranged to facilitate handling of the plate by instruments used to place the prosthesis in use.

* * * * *